United States Patent
Bajic

(10) Patent No.: US 9,618,488 B2
(45) Date of Patent: *Apr. 11, 2017

(54) INTERFACING CAPILLARY ELECTROPHORESIS TO A MASS SPECTROMETER VIA AN IMPACTOR SPRAY IONIZATION SOURCE

(71) Applicant: Micromass UK Limited, Wilmslow (GB)

(72) Inventor: Stevan Bajic, Cheshire (GB)

(73) Assignee: Micromass UK Limited, Wilmslow (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/832,083

(22) Filed: Aug. 21, 2015

(65) Prior Publication Data
US 2015/0355148 A1   Dec. 10, 2015

Related U.S. Application Data

(63) Continuation of application No. 14/367,647, filed as application No. PCT/GB2012/053258 on Dec. 21, 2012, now Pat. No. 9,117,642.
(Continued)

(30) Foreign Application Priority Data

Dec. 23, 2011 (GB) .................................. 1122218.9
Feb. 21, 2012 (GB) .................................. 1202892.4
Oct. 25, 2012 (GB) .................................. 1219217.5

(51) Int. Cl.
*H01J 49/00* (2006.01)
*G01N 30/72* (2006.01)
(Continued)

(52) U.S. Cl.
CPC ... *G01N 30/7266* (2013.01); *G01N 27/44704* (2013.01); *G01N 27/622* (2013.01);
(Continued)

(58) Field of Classification Search
USPC ............ 250/281, 282, 288, 423 R, 424, 425, 250/423 F
See application file for complete search history.

(56) References Cited

U.S. PATENT DOCUMENTS 4,885,076 A    12/1989  Smith et al.
5,877,495 A *   3/1999  Takada ................ H01J 49/0431
                                                       250/288
(Continued)

FOREIGN PATENT DOCUMENTS

JP       10/213569      7/2002
JP       2002190272     7/2002
WO       2009/118775    10/2009

*Primary Examiner* — Nicole Ippolito
*Assistant Examiner* — Hanway Chang
(74) *Attorney, Agent, or Firm* — Diederiks & Whitelaw, PLC

(57) ABSTRACT

A mass spectrometer is disclosed comprising a separation device arranged and adapted to emit an eluent over a period of time. The separation device preferably comprises a Capillary Electrophoresis ("CE") separation device. The mass spectrometer further comprises a nebuliser and a target. Eluent emitted by the separation device is nebulised, in use, by the nebuliser wherein a stream of analyte droplets are directed to impact upon the target so as to ionise the analyte to form a plurality of analyte ions.

19 Claims, 1 Drawing Sheet

Related U.S. Application Data

(60) Provisional application No. 61/580,558, filed on Dec. 27, 2011, provisional application No. 61/601,827, filed on Feb. 22, 2012, provisional application No. 61/718,836, filed on Oct. 26, 2012.

(51) Int. Cl.
*G01N 27/447* (2006.01)
*H01J 49/16* (2006.01)
*G01N 27/62* (2006.01)
*H01J 49/04* (2006.01)
*H01J 49/10* (2006.01)

(52) U.S. Cl.
CPC ........ *H01J 49/0031* (2013.01); *H01J 49/045* (2013.01); *H01J 49/0454* (2013.01); *H01J 49/10* (2013.01); *H01J 49/16* (2013.01); *H01J 49/165* (2013.01)

(56) References Cited

U.S. PATENT DOCUMENTS

| | | |
|---|---|---|
| 7,189,977 B2 | 3/2007 | Yamaguchi et al. |
| 7,335,897 B2 | 2/2008 | Takats et al. |
| 7,368,728 B2 | 5/2008 | Cristoni et al. |
| 7,372,043 B2 | 5/2008 | Joyce et al. |
| 7,465,940 B2 | 12/2008 | Franzen |
| 8,232,520 B2 | 7/2012 | Cristoni |
| 9,117,642 B2 * | 8/2015 | Bajic .................. H01J 49/0454 |
| 2003/0119193 A1 | 6/2003 | Hess et al. |
| 2009/0032135 A1 | 2/2009 | Iida et al. |

* cited by examiner

INTERFACING CAPILLARY ELECTROPHORESIS TO A MASS SPECTROMETER VIA AN IMPACTOR SPRAY IONIZATION SOURCE

CROSS-REFERENCE TO RELATED APPLICATION

This application is a continuation of U.S. patent application Ser. No. 14/367,647 filed 20 Jun. 2014, which is the National Stage of International Application No. PCT/GB2012/053258, filed 21 Dec. 2012, which claims priority from and the benefit of U.S. Provisional Patent Application Ser. No. 61/580,558 filed on 27 Dec. 2011, U.S. Provisional Patent Application Ser. No. 61/601,827 filed on 22 Feb. 2012, U.S. Provisional Patent Application Ser. No. 61/718,836 filed on 26 Oct. 2012, United Kingdom Patent Application No. 1122218.9 filed on 23 Dec. 2011, United Kingdom Patent Application No. 1202892.4 filed on 21 Feb. 2012 and United Kingdom Patent Application No. 1219217.5 filed on 25 Oct. 2012. The entire contents of these applications are incorporated herein by reference.

BACKGROUND TO THE PRESENT INVENTION

Capillary Electrophoresis (CE) is a separation technique where a high voltage is applied to the sample inlet end of a glass capillary column and a lower voltage, or voltage of opposite polarity, is applied to the outlet end of the capillary. Analytes elute from the column at a rate that is determined by a combination of electroosmotic flow and the electrophoretic mobility of the analytes. Since the electroosmotic flow velocity can exceed the electrophoretic drift velocity of ions, it is possible to analyse both positive and negative ions in the same chromatographic separation. In such circumstances, the elution order can be generalized as multiply charged positive ions emerging first, followed by singly charged positive ions, followed by neutral analytes, followed by singly charged negative ions and finally followed by multiply charged negative ions. Commonly used CE detectors such as UV and fluorescence devices can analyse both ion polarities in a single chromatographic run.

However, when interfacing CE to mass spectrometry via an Electrospray ionization source, the column outlet is located at the Electrospray probe tip which in turn, is biased to typically 3 kV via a separate high voltage supply and a potential divider circuit. The analysis of positive and negative ions requires ESI tip voltages of +3 kV and −3 kV respectively. This precludes the use of fast positive/negative switching in a single chromatographic run since this would affect the total CE voltage and hence electroosmotic and electrophoretic flows.

Another disadvantage of the conventional arrangement is that biasing the ESI tip requires the additional cost of an ESI power supply circuit. Furthermore, such an arrangement imposes limitations on buffer concentration and ESI voltage stability.

It is therefore desired to provide an improved mass spectrometer.

SUMMARY OF THE PRESENT INVENTION

According to an aspect of the present invention there is provided a mass spectrometer comprising:

a separation device arranged and adapted to emit an eluent over a period of time, wherein the separation device comprises either: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device;

a nebuliser and;

a target;

wherein the eluent emitted by the separation device is nebulised, in use, by the nebuliser wherein a stream of analyte droplets are directed to impact upon the target so as to ionise the analyte to form a plurality of analyte ions.

The present invention is particularly advantageous in that a Capillary Electrophoresis ("CE") separation device and other types of separation device may be arranged to emit an eluent which is then nebulised so that a resulting stream of droplets is then ionised upon impacting a target. Interfacing a CE separation device to an impact ionisation source according to the present invention is particularly advantageous since the conventional teaching is to interface a CE separation device to an Electrospray ionisation source. However, this involves maintaining the Electrospray probe tip at +3 kV and being able rapidly to switch the probe tip to −3 kV in order to produce negative ions. It is problematic to maintain the Electrospray probe tip at 3 kV when coupled to a CE separation device and it is not possible to rapidly switch the voltage of the probe tip as this would affect the total CE voltage and hence the electroosmotic and electrophoretic flows.

The present invention, therefore, enables the probe tip to be maintained e.g. at ground potential and avoids the expense and added complication of requiring a fast switching high voltage power supply for the probe.

The present invention wherein a CE separation device is coupled with an impact ionisation ion source is, therefore, particularly advantageous compared to conventional arrangement wherein a CE separation device is interfaced with a high voltage Electrospray ionisation ion source.

According to a preferred embodiment of the present invention the liquid flow from the outlet of a capillary electrophoresis column is connected to the inner capillary of a grounded, tri-axial, pneumatic nebuliser probe. A flow of make-up solution is added to the second concentric capillary which mixes with the flow from the inner capillary at the probe tip. The resulting liquid stream is converted into a nebulised spray via a concentric flow of high velocity gas from a third concentric capillary. A small impactor target is preferably positioned in relatively close proximity to the nebuliser tip to define an impact zone and to ionize the incoming high velocity droplet stream. The resulting ions and charged droplets are sampled by a first vacuum stage of a mass spectrometer.

The ionizing high voltage is decoupled from the probe tip and a grounded probe assembly can advantageously be utilised which acts as a stable reference for the applied CE voltage. This is particularly advantageous compared to conventional arrangements.

The nebuliser probe tip is preferably held at (or relatively close to) ground potential whilst any high voltage for ionization is preferably held on an impactor target that is positioned a short distance from the tip. This arrangement eliminates the problems described above and enables the use of fast polarity switching of the impactor target to analyse both positive and negative ions in a single CE/MS run.

The impactor spray source may generally operate at liquid flow rates ≤1 μL/min. However, since the electroosmotic flow associated with a CE column is extremely low (<<1

μL/min), the impactor spray nebuliser probe is preferably constructed with a triaxial probe arrangement that increases the total liquid flow rate. An inner capillary is preferably connected to the outlet of a CE capillary column. The inner capillary is preferably surrounded by a second concentric capillary that preferably delivers a make-up flow of liquid that mixes with the liquid flow from the CE column. The second capillary is preferably surrounded by a third concentric capillary which preferably delivers high velocity nitrogen gas to nebulise the resulting liquid flows from the other two capillaries. All three capillaries in the tri-axial arrangement are preferably maintained at ground potential. An impactor target is preferably held at a relatively high potential and is preferably positioned in relatively close proximity to the probe tip.

According to a preferred embodiment the liquid flow from the outlet of a capillary electrophoresis column is connected to the inner capillary of grounded, preferably tri-axial, pneumatic nebuliser probe. A flow of make-up solution is added to the second concentric capillary which mixes with the flow from the inner capillary at the probe tip. The resulting liquid stream is converted into a nebulised spray via a concentric flow of high velocity gas from a third concentric capillary. A small impactor target is positioned in close proximity to the nebuliser tip to define an impact zone and to ionize the incoming high velocity droplet stream. The resulting ions and charged droplets are sampled by the first vacuum stage of a mass spectrometer.

The preferred embodiment alleviates interfacing problems by decoupling the ionizing high voltage from the probe tip and instead preferably utilizing a grounded probe assembly which acts as a stable reference for the applied CE voltage. In Impactor Spray ionization, the nebuliser probe tip is preferably held at ground potential whilst any high voltage for ionization is preferably held on an impactor target that is preferably positioned a short distance from the tip. This arrangement eliminates the problems described above and enables the use of fast polarity switching of the impactor target to analyse both positive and negative ions in a single CE/MS run.

High voltage ESI nebuliser probes can complicate interfacing MS sources with high voltage chromatography techniques such as CE and CEC. The preferred embodiment solves the problem of creating ionization without applying a high voltage directly to the nebuliser probe.

The separation device preferably comprises a Capillary Electrophoresis ("CE") separation device wherein an inlet end of the Capillary Electrophoresis separation device is maintained at a first potential and an outlet end of the Capillary Electrophoresis separation device is maintained at a second potential.

The separation device preferably comprises or is coupled to a first tube.

The first tube preferably comprises a capillary tube.

The exit of the first tube is preferably maintained, in use, at a potential (i) −5 to −4 kV; (ii) −4 to −3 kV; (iii) −3 to −2 kV; (iv) −2 to −1 kV; (v) −1000 to −900 V; (vi) −900 to −800 V; (vii) −800 to −700 V; (viii) −700 to −600 V; (ix) −600 to −500 V; (x) −500 to −400 V; (xi) −400 to −300 V; (xii) −300 to −200 V; (xiii) −200 to −100 V; (xiv) −100 to −90 V; (xv) −90 to −80 V; (xvi) −80 to −70 V; (xvii) −70 to −60 V; (xviii) −60 to −50 V; (xix) −50 to −40 V; (xx) −40 to −30 V; (xxi) −30 to −20 V; (xxii) −20 to −10 V; (xxiii) −10 to 0V; (xxiv) 0-10 V; (xxv) 10-20 V; (xxvi) 20-30 V; (xxvii) 30-40V; (xxviii) 40-50 V; (xxix) 50-60 V; (xxx) 60-70 V; (xxxi) 70-80 V; (xxxii) 80-90 V; (xxxiii) 90-100 V; (xxxiv) 100-200 V; (xxxv) 200-300 V; (xxxvi) 300-400 V; (xxxvii) 400-500 V; (xxxviii) 500-600 V; (xxxix) 600-700 V; (xl) 700-800 V; (xli) 800-900 V; (xlii) 900-1000 V; (xliii) 1-2 kV; (xliv) 2-3 kV; (xlv) 3-4 kV; and (xlvi) 4-5 kV.

According to a less preferred embodiment the exit of the first tube may be maintained at a potential <−5 kV or >5 kV.

The first tube is preferably surrounded by a second tube which is arranged and adapted to provide a flow of liquid which mixes with the eluent emerging from the exit of the first tube.

The second tube preferably comprises a capillary tube.

The ends of the first and second tubes may be either: (i) flush or parallel with each other; or (ii) protruded, recessed or non-parallel relative to each other.

The mass spectrometer preferably comprises a third tube which may surround the second tube and which is arranged and adapted to provide a stream of gas to the exit of the first tube and/or the second tube.

The third tube preferably comprises a capillary tube.

The third tube preferably surrounds the second tube and/or is concentric with the first and second tubes.

According to an embodiment the ends of the first, second and third tubes may be either: (i) flush or parallel with each other; or (ii) protruded, recessed or non-parallel relative to each other.

According to an alternative embodiment the third tube may be non-concentric with the first and the second tubes.

The mass spectrometer preferably further comprises a heater which is arranged and adapted to supply a heated stream of gas to heat droplets emerging from the first tube and/or the second tube.

The target is preferably arranged <10 mm, <9 mm, <8 mm, <7 mm, <6 mm, <5 mm, <4 mm, <3 mm or <2 mm from the exit of the nebuliser.

The target is preferably maintained, in use, at a potential (i) −5 to −4 kV; (ii) −4 to −3 kV; (iii) −3 to −2 kV; (iv) −2 to −1 kV; (v) −1000 to −900 V; (vi) −900 to −800 V; (vii) −800 to −700 V; (viii) −700 to −600 V; (ix) −600 to −500 V; (x) −500 to −400 V; (xi) −400 to −300 V; (xii) −300 to −200 V; (xiii) −200 to −100 V; (xiv) −100 to −90 V; (xv) −90 to −80 V; (xvi) −80 to −70 V; (xvii) −70 to −60 V; (xviii) −60 to −50 V; (xix) −50 to −40 V; (xx) −40 to −30 V; (xxi) −30 to −20 V; (xxii) −20 to −10 V; (xxiii) −10 to 0V; (xxiv) 0-10 V; (xxv) 10-20 V; (xxvi) 20-30 V; (xxvii) 30-40V; (xxviii) 40-50 V; (xxix) 50-60 V; (xxx) 60-70 V; (xxxi) 70-80 V; (xxxii) 80-90 V; (xxxiii) 90-100 V; (xxxiv) 100-200 V; (xxxv) 200-300 V; (xxxvi) 300-400 V; (xxxvii) 400-500 V; (xxxviii) 500-600 V; (xxxix) 600-700 V; (xl) 700-800 V; (xli) 800-900 V; (xlii) 900-1000 V; (xliii) 1-2 kV; (xliv) 2-3 kV; (xlv) 3-4 kV; and (xlvi) 4-5 kV.

According to a less preferred embodiment the target may be maintained at a potential <−5 kV or >5 kV.

The mass spectrometer further comprises a control system, wherein the control system is arranged and adapted either: (i) to switch the polarity of said target during a single experimental run; or (ii) to repeatedly switch the polarity of the target during a single experimental run.

According to an embodiment the control system may be arranged and adapted to repeatedly switch the polarity of said target every 0-10 ms, 10-20 ms, 20-30 ms, 30-40 ms, 40-50 ms, 50-60 ms, 60-70 ms, 70-80 ms, 80-90 ms, 90-100 ms, 100-200 ms, 200-300 ms, 300-400 ms, 400-500 ms, 500-600 ms, 600-700 ms, 700-800 ms, 800-900 ms, 900-1000 ms, 1-2 s, 2-3 s, 3-4 s or 4-5 s.

According to another embodiment the control system may utilise retention time switching. According to an embodiment the polarity of the target may be repeatedly switched once every 0-1 mins, 1-2 mins, 2-3 mins, 3-4 mins, 4-5 mins, 5-6 mins, 6-7 mins, 7-8 mins, 8-9 mins, 9-10 mins or >10 mins.

The mass spectrometer preferably further comprises an enclosure enclosing the nebuliser, the target and an ion inlet device which leads to a first vacuum stage of the mass spectrometer.

According to an embodiment the ion inlet device may comprise an ion orifice, an ion inlet cone, an ion inlet capillary, an ion inlet heated capillary, an ion tunnel, an ion mobility spectrometer or separator, a differential ion mobility spectrometer, a Field Asymmetric Ion Mobility Spectrometer ("FAIMS") device or other ion inlet.

The exit of the first tube preferably has a diameter D and the spray of analyte droplets is preferably arranged to impact on an impact zone of the target.

The impact zone preferably has a maximum dimension of x and wherein the ratio x/D is in the range <2, 2-5, 5-10, 10-15, 15-20, 20-25, 25-30, 30-35, 35-40 or >40.

The impact zone preferably has an area selected from the group consisting of: (i)<0.01 mm$^2$; (ii) 0.01-0.10 mm$^2$; (iii) 0.10-0.20 mm$^2$; (iv) 0.20-0.30 mm$^2$; (v) 0.30-0.40 mm$^2$; (vi) 0.40-0.50 mm$^2$; (vii) 0.50-0.60 mm$^2$; (viii) 0.60-0.70 mm$^2$; (ix) 0.70-0.80 mm$^2$; (x) 0.80-0.90 mm$^2$; (xi) 0.90-1.00 mm$^2$; (xii) 1.00-1.10 mm$^2$; (xiii) 1.10-1.20 mm$^2$; (xiv) 1.20-1.30 mm$^2$; (xv) 1.30-1.40 mm$^2$; (xvi) 1.40-1.50 mm$^2$; (xvii) 1.50-1.60 mm$^2$; (xviii) 1.60-1.70 mm$^2$; (xix) 1.70-1.80 mm$^2$; (xx) 1.80-1.90 mm$^2$; (xxi) 1.90-2.00 mm$^2$; (xxii) 2.00-2.10 mm$^2$; (xxiii) 2.10-2.20 mm$^2$; (xxiv) 2.20-2.30 mm$^2$; (xxv) 2.30-2.40 mm$^2$; (xxvi) 2.40-2.50 mm$^2$; (xxvii) 2.50-2.60 mm$^2$; (xxviii) 2.60-2.70 mm$^2$; (xxix) 2.70-2.80 mm$^2$; (xxx) 2.80-2.90 mm$^2$; (xxxi) 2.90-3.00 mm$^2$; (xxxii) 3.00-3.10 mm$^2$; (xxxiii) 3.10-3.20 mm$^2$; (xxxiv) 3.20-3.30 mm$^2$; (xxxv) 3.30-3.40 mm$^2$; (xxxvi) 3.40-3.50 mm$^2$; (xxxvii) 3.50-3.60 mm$^2$; (xxxviii) 3.60-3.70 mm$^2$; (xxxix) 3.70-3.80 mm$^2$; (xl) 3.80-3.90 mm$^2$; and (xli) 3.90-4.00 mm$^2$.

The target is preferably located at a first distance $X_1$ in a first direction from an ion inlet device which leads to a first vacuum stage of the mass spectrometer and at a second distance $Z_1$ in a second direction from the ion inlet device, wherein the second direction is orthogonal to the first direction and wherein:

(i) $X_1$ is selected from the group consisting of: (i) 0-1 mm; (ii) 1-2 mm; (iii) 2-3 mm; (iv) 3-4 mm; (v) 4-5 mm; (vi) 5-6 mm; (vii) 6-7 mm; (viii) 7-8 mm; (ix) 8-9 mm; (x) 9-10 mm; and (xi) >10 mm; and/or (ii) $Z_1$ is selected from the group consisting of: (i) 0-1 mm; (ii) 1-2 mm; (iii) 2-3 mm; (iv) 3-4 mm; (v) 4-5 mm; (vi) 5-6 mm; (vii) 6-7 mm; (viii) 7-8 mm; (ix) 8-9 mm; (x) 9-10 mm; and (xi) >10 mm.

The target is preferably positioned so as to deflect the stream of analyte droplets and/or the plurality of analyte ions towards an ion inlet device of the mass spectrometer.

According to an embodiment the ion inlet device may comprise an ion orifice, an ion inlet cone, an ion inlet capillary, an ion inlet heated capillary, an ion tunnel, an ion mobility spectrometer or separator, a differential ion mobility spectrometer, a Field Asymmetric Ion Mobility Spectrometer ("FAIMS") device or other ion inlet.

The target is preferably positioned upstream of an ion inlet device of the mass spectrometer so that ions are deflected towards the direction of the ion inlet device.

The target preferably comprises either: (i) a rod; or (ii) a pin having a taper cone;

wherein the stream of analyte droplets is arranged to impact the rod or the taper cone of the pin either: (i) directly on the centerline of the rod or pin; or (ii) on the side of the rod or the taper cone which faces towards or away from an ion inlet orifice of the mass spectrometer.

The ion source preferably comprises an Atmospheric Pressure Ionisation ("API") ion source.

The target preferably comprises a stainless steel target, a metal, gold, a non-metallic substance, a semiconductor, a metal or other substance with a carbide coating, an insulator or a ceramic.

According to an embodiment the target may comprise a plurality of plates so that droplets from the nebuliser cascade upon a plurality of target plates and/or wherein the target is arranged to have multiple impact points so that droplets are ionised by multiple glancing deflections.

According to an embodiment the target comprises one or more mesh or grid targets.

A grid or mesh target having a grid or mesh impaction surface has been found to be particularly advantageous compared with using a pin target since utilising a grid or mesh target solves the problem of positional dependence which may otherwise be experienced when using a solid pin as the target.

The one or more mesh or grid targets preferably comprise one or more wire mesh or grid targets.

The wire mesh or grid target preferably comprise wire having a diameter selected from the group consisting of: (i)<50 μm; (ii) 50-100 μm; (iii) 100-150 μm; (iv) 150-200 μm; (v) 200-250 μm; (vi) 250-300 μm; (vii) 300-350 μm; (viii) 350-400 μm; (ix) 400-450 μm; (x) 450-500 μm; (xi) 500-550 μm; (xii) 550-600 μm; (xiii) 600-650 μm; (xiv) 650-700 μm; (xv) 700-750 μm; (xvi) 750-800 μm; (xvii) 800-850 μm; (xviii) 850-900 μm; (xix) 900-950 μm; (xx) 950-1000 μm; and (xxi) >1 mm.

The mesh or grid preferably has a spacing selected from the group consisting of: (i)<50 μm; (ii) 50-100 μm; (iii) 100-150 μm; (iv) 150-200 μm; (v) 200-250 μm; (vi) 250-300 μm; (vii) 300-350 μm; (viii) 350-400 μm; (ix) 400-450 μm; (x) 450-500 μm; (xi) 500-550 μm; (xii) 550-600 μm; (xiii) 600-650 μm; (xiv) 650-700 μm; (xv) 700-750 μm; (xvi) 750-800 μm; (xvii) 800-850 μm; (xviii) 850-900 μm; (xix) 900-950 μm; (xx) 950-1000 μm; and (xxi) >1 mm.

The one or more mesh or grid targets are preferably arranged in a plane which is either: (i) substantially perpendicular to a spray axis of the one or more nebulisers; or (ii) inclined at an angle <90° to a spray axis of the one or more nebulisers.

The one or more mesh or grid targets preferably provide multiple impact zones.

The one or more mesh or grid targets preferably comprise a 1-dimensional or a 2-dimensional array of interstices or openings.

The one or more mesh or grid targets preferably comprise a plurality of layers.

One or more of the layers preferably comprises a mesh or grid.

The plurality of layers preferably comprise layers having substantially the same or substantially different mesh sizes.

According to an embodiment the mass spectrometer further comprises a vibration device arranged and adapted to cause the target to vibrate.

The use of piezoelectric vibration applied to the impactor bar or target is particularly advantageous in that vibrating the target aids in the reduction of resultant secondary droplets through surface disruption. The use of piezoelectric vibration is also particularly advantageous in that it also reduces liquid beading.

The vibration source is preferably arranged and adapted to cause the target to vibrate in order to reduce the size of resultant secondary droplets through surface disruption.

The vibration source preferably comprises a piezo-electric vibration source.

The vibration source is preferably arranged and adapted to vibrate the target at a frequency f selected from the group consisting of: (i)<1 kHz; (ii) 1-2 kHz; (iii) 2-3 kHz; (iv) 3-4 kHz; (v) 4-5 kHz; (vi) 5-6 kHz; (vii) 6-7 kHz; (viii) 7-8 kHz; (ix) 8-9 kHz; (x) 9-10 kHz; (xi) 10-11 kHz; (xii) 11-12 kHz; (xiii) 12-13 kHz; (xiv) 13-14 kHz; (xv) 14-15 kHz; (xvi) 15-16 kHz; (xvii) 16-17 kHz; (xviii) 17-18 kHz; (xix) 18-19 kHz; (xx) 19-20 kHz; and (xxi) >20 kHz.

According to an embodiment the mass spectrometer preferably further comprises a first device arranged and adapted to rotate and/or translate the target.

As will be understood by those skilled in the art the positioning of the target is important in order to obtain an acceptable level of signal intensity when generating ions by impacting high velocity droplets onto the target. According to a particularly preferred embodiment causing the target to rotate (e.g. on an eccentric path) relative to the spray of high velocity droplets enables an average more stable signal intensity to be realised. As a result, the overall or average ion signal can be stabilised and is less susceptible to wide variations in the intensity of analyte ions generated which depends upon the precise position of the target relative to the high velocity spray of droplets.

The target preferably comprises a pin or rod.

The target preferably has a first central longitudinal axis and the first device is arranged and adapted to rotate the target about a second axis which is displaced or offset from the first axis.

The first device is preferably arranged and adapted to cause the target to rotate, in use, about or on a substantially eccentric or non-circular path.

The first device is preferably arranged and adapted to rotate the target at a rate of: (i)<1 rev/s; (ii) 1-2 rev/s; (iii) 2-3 rev/s; (iv) 3-4 rev/s; (v) 4-5 rev/s; (vi) 5-6 rev/s; (vii) 6-7 rev/s; (viii) 7-8 rev/s; (ix) 8-9 rev/s; (x) 9-10 rev/s; (xi) >10 rev/s; (xii)<1 rpm; (xiii) 1-5 rpm; (xiv) 5-10 rpm; (xv) 10-15 rpm; (xvi) 15-20 rpm; (xvii) 20-25 rpm; (xviii) 25-30 rpm; (xix) 30-35 rpm; (xx) 35-40 rpm; (xxi) 40-45 rpm; (xxii) 45-50 rpm; (xxiii) 50-60 rpm; (xxiv) 60-70 rpm: (xxv) 70-80 rpm; (xxvi) 80-90 rpm; (xxvii) 90-100 rpm; (xxviii) 100-150 rpm; (xxix) 150-200 rpm; (xxx) 200-250 rpm; and (xxxi) >250 rpm.

The first device is preferably arranged and adapted to rotate the target substantially continuously.

The first device is preferably arranged and adapted to rotate the target substantially continuously for at least a period T, wherein T is selected from the group consisting of: (i)<1 s; (ii) 1-5 s; (iii) 5-10 s; (iv) 10-15 s; (v) 15-20 s; (vi) 20-25 s; (vii) 25-30 s; (viii) 30-35 s; (ix) 35-40 s; (x) 40-45 s; (xi) 45-50 s; (xii) 50-55 s; (xiii) 55-60 s; and (xiv) >60 s.

The mass spectrometer preferably comprises a control system arranged and adapted to monitor an analyte signal as a function of or in respect of the position of the target.

The control system is preferably arranged and adapted to cause a device to rotate and/or translate the target to a desired position in order to optimise an analyte ion signal or to otherwise control the intensity of analyte ions.

The control system is preferably arranged and adapted to cause a device to rotate and/or translate the target between a plurality of desired positions in order to vary or control the intensity of analyte ions.

According to an aspect of the present invention there is provided a method of mass spectrometry comprising:

providing a separation device arranged and adapted to emit an eluent over a period of time, wherein the separation device comprises either: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device;

providing a target; and nebulising the eluent emitted by the separation device wherein a stream of analyte droplets are directed to impact upon the target so as to ionise the analyte to form a plurality of analyte ions.

According to an embodiment the mass spectrometer may further comprise:

(a) an additional ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; and (xxi) an Impactor ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic or orbitrap mass analyser; (x) a Fourier Transform electrostatic or orbitrap mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometer may further comprise either:

(i) a C-trap and an Orbitrap® mass analyser comprising an outer barrel-like electrode and a coaxial inner spindle-like electrode, wherein in a first mode of operation ions are transmitted to the C-trap and are then injected into the Orbitrap® mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the Orbitrap® mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

BRIEF DESCRIPTION OF THE DRAWINGS

Various embodiments of the present invention will now be described, by way of example only, and with reference to the accompanying drawings in which.

DETAILED DESCRIPTION OF PREFERRED EMBODIMENT

Figure 1:
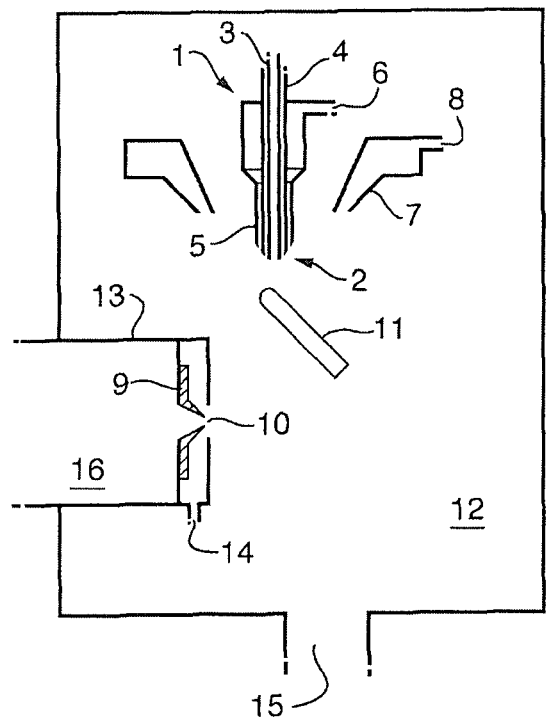
FIG. 1 shows an impactor spray API source according to an embodiment of the present invention.

FIG. 1 is a schematic of the general layout of an impactor spray API source according to a preferred embodiment. A flow of liquid from a CE column outlet (or other separation device) enters a nebuliser probe 1 and is delivered to a sprayer tip 2 via an inner capillary tube 3. The inner capillary 3 is surrounded by a second concentric capillary 4 which delivers a make-up flow of liquid which mixes with the flow from the first capillary 3 at the probe tip. The second capillary tube 4 is surrounded by a third concentric capillary 5 which includes a gas inlet 6 to deliver a stream of high velocity gas to the exit of the liquid capillaries 3,4.

This arrangement produces a nebulised spray which contains droplets with a typical diameter of 10-20 μm and velocities greater than 100 m/s at a close distance from the sprayer tip 2. The resulting droplets are heated by an additional flow of gas that enters a concentric annular heater 7 via a second gas inlet 8.

The sprayer is preferably hinged to the right hand side of an ion inlet cone 9 of the mass spectrometer and can swing to vary the horizontal distance between the sprayer tip 2 and an ion inlet orifice 10 of a mass spectrometer. The probe is also configured such that the vertical distance between the sprayer tip 2 and the ion inlet orifice 10 can be varied. The relative tip positions of the inner capillary 3, the second capillary 4 and the third capillary 5 can be adjusted. According to an embodiment the capillaries 3,4,5 may be arranged so that they are flush with one another. According to another embodiment the capillaries 3,4,5 may be arranged so that one or more capillaries 3,4,5 protrude or are recessed relative to each other.

A target 11 with a similar dimension to the liquid capillary is preferably placed between the sprayer tip 2 and the ion inlet orifice 10. The target 11 can be manipulated in the x and y directions (in the horizontal plane) via a micro adjuster stage and can be held at a potential of typically 0-5 kV relative to the source enclosure 12 and the ion inlet orifice 10. In operation, the ion inlet cone 10 is surrounded by a metal cone gas housing 13 that is flushed with a low flow of nitrogen gas that enters via a gas inlet 14. All gasses that enter the source enclosure must leave via the source enclosure exhaust 15 or the ion inlet orifice 10 which is pumped by the first vacuum stage 16 of the mass spectrometer.

Figure 2A:
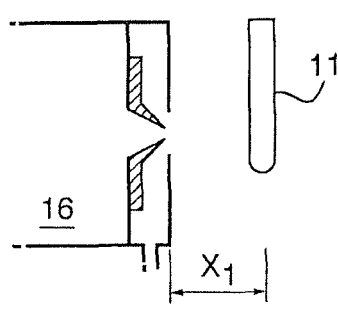
FIG. 2A shows an impactor spray source and FIG. 2B shows an optimised impactor spray source.

FIG. 2A is a schematic plan view of an impactor spray source with the grounded nebuliser probe omitted from the diagram. The impactor target 11 comprises a stainless steel rod or pin with an outside diameter of typically 1-2 mm. The rod or pin 11 is positioned at a horizontal distance $X_1$ of typically 5 mm from the ion inlet orifice 10. The probe tip can be finely adjusted to sweep across the target surface until the optimum impact point is found that gives the greatest sensitivity. A typical optimized position is shown in the schematic of FIG. 2B where the offset $X_2$ is approximately 0.4 mm.

Figure 2B:
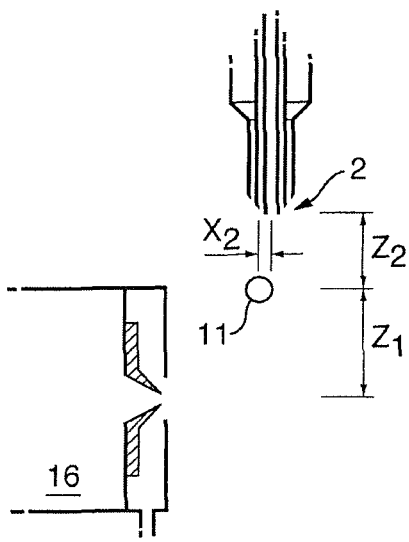

FIG. 2B also shows the vertical positions of the probe and target in the preferred embodiment, i.e. $Z_1$=9 mm and $Z_2$=3 mm.

In the preferred embodiment, the source is operated with the following bias potentials: nebuliser=0V, impactor target=1.0 kV, ion inlet cone=100 V and cone gas housing=100

V. The heater assembly and source enclosure are preferably maintained at ground potential. The source may be operated with the following gas flow settings: nitrogen nebulizer gas pressurized to 7 bar, nitrogen heater gas flow=1200 L/hr and nitrogen cone gas flow=150 L/hr.

The preferred embodiment can be used in other applications that are similarly simplified by the use of a grounded nebuliser probe such as capillary electrochromatography (CEC) and tile-based microchip LC/MS systems.

The tile-based microchip LC system preferably comprises a substantially rigid ceramic-based multilayer microfluidic substrate also referred to as a "ceramic tile". Reference is made to US 2009/032135 the contents of which are incorporated herein by reference. For a protein sample the ceramic may comprise a High-Temperature Co-fired Ceramic (HTCC) which provides suitably low levels of loss of sample due to attachment of sample to walls of conduits in the substrate. Formed in the layers of the substrate is a channel that operates as a separation column. Apertures in the side of the substrate provide openings into the channel through which fluid may be introduced into the column. Fluid passes through the apertures under high pressure and flows toward the Electrospray emitter coupled at the egress end of the channel. Holes in the side of a microfluidic cartridge provide fluidic inlet ports for delivering the fluid to the substrate. Each fluidic inlet port aligns with and encircles one of the fluidic apertures.

The preferred embodiment may also be implemented as an interface for supercritical fluid chromatography/MS.

Impaction-based spray using a target pin has been shown to provide improved ionization efficiency for both polar and non-polar compounds compared to standard ESI or APCI. However, the performance with different mobile phase compositions has sometimes been observed to have a reasonably strong dependence upon the physical geometry of the probe and pin.

The positional dependence of the probe and pin on the relative performance at high organic mobile phase can make achieving required tolerances problematic. Furthermore, maintaining these tolerances can also be problematic since the pin and/or probe capillary may need to be replaced one or more times during the lifetime of the instrument.

According to an embodiment of the present invention a grid or mesh target is preferably used instead of a pin target. A grid or mesh target having a grid or mesh impaction surface has been found to be particularly advantageous compared with using a pin target in that utilising a grid or mesh target solves the problem of positional dependence which may otherwise be experienced when using a solid pin as the target.

A mesh or grid target of appropriate size is preferably used as the impact target. According to the preferred embodiment the impact zone (i.e. the diameter of the plume at point of impact with the target) is preferably 0.5-1.0 mm.

According to the preferred embodiment the mesh wire size and spacing is preferably sized appropriately so as to provide several discrete impact zones within the impact zone or area. The wire diameter is preferably sufficient so as to allow the impact of the plume on the wire to improve nebulisation. A mesh with 150 μm spacing and a wire diameter of 100 μm has been found to be particularly advantageous. However, other aspect ratios are also contemplated and are intended to fall within the scope of the present invention. According to an embodiment the mesh or grid may comprise a substantially flat rectangle (15 mm×7 mm) and may be held substantially perpendicular to the spray axis. According to this embodiment the spray is essentially through the mesh or grid.

Alternatively, the mesh or grid may be angled relative to the spray axis. The angle of the mesh or grid may be set such that the plume as it passes through the mesh or grid is deflected close to or in the direction of the mass spectrometer inlet. The mesh or grid target may be arranged at an angle of 70° relative to the spray axis.

The physical dimensions of the mesh or grid are preferably set or arranged so that liquid beading on the surface of the mesh or grid is preferably minimized. The angle and shape of the mesh or grid may be optimised to reduce liquid beading.

According to the preferred embodiment a high voltage may be applied to the mesh or grid electrode in order to assist ionization in a similar manner to other embodiments of the present invention which have been described above and which utilise a pin target. According to an embodiment the mesh or grid may be maintained at a potential of 1 kV. However, it will be apparent to those skilled in the art that the mesh or grid target may be maintained at other potentials.

A particular advantage of using a mesh or grid target is that the mesh or grid target according to the preferred embodiment shows a significantly reduced dependence on positional geometry since the stream of droplets impacts upon multiple impaction points on the mesh or grid target. As the probe or mesh target is moved, the characteristics of the impact of the droplets upon the target remain substantially the same. Accordingly, the performance of the ion source relative to the position of the MS inlet and the probe behaves in a similar manner to an Electrospray ionisation ("ESI") ion source relative to an ion inlet.

Further embodiments are also contemplated. For example, a grid instead of a mesh may be used. The grid preferably has multiple impaction points in the zone in which the stream of droplets impacts upon the target. If positional dependence of the spray direction after impact is required then a single-row grid may be utilised.

According to an embodiment the target may comprise multiple layers of meshes and/or grids in order to achieve the same effect as angling a single layered mesh or grid target.

According to an embodiment the surface ionization impactor bar or target as described above may be further enhanced by utilising a piezoelectric vibration device to vibrate the bar or target. Vibration of the bar or target upon which the surface ionization occurs aids in the reduction of the size of the secondary droplets, increasing the evaporation rate of the solvent and thereby aids signal response.

According to a preferred embodiment an impactor bar or target is located within a source enclosure. In this configuration the capillary is preferably grounded and potentials are preferably applied to the impactor bar or target and to the sample cone inlet structure. The integration of an impactor spray with a separation device introduces the potential for the generation of non-polar, highly polar, singularly charged and/or multiply charged gas phase ions for introduction into the mass spectrometer for analysis. The ionization processes and flow dynamics may, however, be different which can result in the formation of larger sized droplets. The use of piezoelectric vibration applied to the impactor bar or target is particularly advantageous in that it aids in the reduction of resultant secondary droplets.

It will be understood by those skilled in the art that the mechanisms of droplet production in pneumatically assisted nebulisation are non-trivial and it cannot be approximated by a particular model for which the boundary conditions are known. There is no single process that is believed to be solely responsible for droplet production and the initial spray produced is rapidly modified by secondary fragmentation and by recombination and coalescence. The use of piezoelectric vibration applied to the impactor bar or target preferably aids in the reduction of the resultant secondary droplets through surface disruption.

According to an embodiment a target pin is preferably utilised which is preferably rotated on e.g. an eccentric path so as to obtain an easily reproducible level of ion signal. According to an embodiment a target pin or rod is preferably placed or mounted off axis on a rotating shaft. The pin or rod target is preferably located or arranged so as to be in the path of high velocity droplets emitted from a sprayer. The droplets emitted from the sprayer are arranged to impact upon the pin or rod target so as to produce ions for analysis by mass spectrometry. The rotational position of the pin or rod is preferably controlled through a motor under computer control.

According to an embodiment the analyte signal may be monitored with respect to the position of the pin or rod. The pin or rod may then be rotated or otherwise set to a particular position under computer control in order to maximise the signal intensity. Other embodiments are also contemplated wherein the pin or rod may be rotated between one or more different rotational positions in order to control the intensity of analyte ions produced or to control the efficiency of analyte ion production.

The central longitudinal axis of the pin or rod is preferably arranged so as to be off centre relative to the central longitudinal axis of the rotating shaft. The position of the pin or rod may according to an embodiment vary by approximately 0.7 mm during the course of one rotation of the pin or rod target.

According to a less preferred embodiment the position of the pin or rod target 10 may be translated rather than rotated (or the pin or rod target may be translated in addition to being rotated).

As will be understood by those skilled in the art the positioning of the target is important in order to obtain an acceptable level of signal intensity when generating ions by impacting high velocity droplets onto the target. According to a particularly preferred embodiment causing the target to rotate on an eccentric path relative to the spray of high velocity droplets enables an average signal intensity to be realised. As a result, the overall or average ion signal can be stabilised and is less susceptible to wide variations in the intensity of analyte ions generated depending upon the precise position of the target relative to the high velocity spray of droplets.

Although the present invention has been described with reference to preferred embodiments, it will be understood by those skilled in the art that various changes in form and detail may be made without departing from the scope of the invention as set forth in the accompanying claims.

The invention claimed is:

1. A mass spectrometer comprising:
   a separation device arranged and adapted to emit an eluent over a period of time, wherein said separation device comprises either: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device;
   a nebuliser and;
   a target;
   wherein said eluent emitted by said separation device is nebulised, in use, by said nebuliser wherein a stream of analyte droplets are directed to impact upon said target so as to ionise said analyte to form a plurality of analyte ions.

2. A mass spectrometer as claimed in claim 1, wherein the substantially rigid ceramic-based multilayer microfluidic substrate separation device comprises a High-Temperature Co-fired Ceramic ("HTCC").

3. A mass spectrometer as claimed in claim 1, wherein the nebuliser is constructed with a tri-axial probe arrangement.

4. A mass spectrometer as claimed in claim 1, wherein said separation device comprises or is coupled to a first tube.

5. A mass spectrometer as claimed in claim 4, wherein said first tube comprises a capillary tube.

6. A mass spectrometer as claimed in claim 4, wherein said first tube is surrounded by a second tube which is arranged and adapted to provide a flow of liquid which mixes with the eluent emerging from the exit of said first tube.

7. A mass spectrometer as claimed in claim 6, wherein said second tube comprises a capillary tube.

8. A mass spectrometer as claimed in claim 7, further comprising a third tube which is arranged and adapted to provide a stream of gas to the exit of said first tube or said second tube.

9. A mass spectrometer as claimed in claim 8, wherein said third tube comprises a capillary tube.

10. A mass spectrometer as claimed in claim 8, wherein said third tube surrounds said second tube or is concentric with said first and second tubes.

11. A mass spectrometer as claimed in claim 8, wherein said third tube is non-concentric with said first and said second tubes.

12. A mass spectrometer as claimed in claim 1, wherein said target comprises one or more mesh or grid targets.

13. A method of mass spectrometry comprising:
    providing a separation device arranged and adapted to emit an eluent over a period of time, wherein said separation device comprises either: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device;
    providing a target; and
    nebulising said eluent emitted by said separation device wherein a stream of analyte droplets are directed to impact upon said target so as to ionise said analyte to form a plurality of analyte ions.

14. A method of mass spectrometry as claimed in claim 13, further comprising delivering a make-up flow of liquid that mixes with the liquid flow from the separation device.

15. A method of mass spectrometry as claimed in claim 13, wherein a flow of liquid from the separation device enters a nebuliser probe and is delivered to a sprayer tip via a first tube.

16. A method of mass spectrometry as claimed in claim 15, wherein the first tube is surrounded by a second tube which delivers a make-up flow of liquid which mixes with the flow from the first tube at the probe tip.

17. A method of mass spectrometry as claimed in claim 16, wherein the second tube is surrounded by a third tube which includes a gas inlet to deliver a stream of high velocity gas to the exit of the first and second tubes.

18. A mass spectrometer comprising:
a separation device arranged and adapted to emit an eluent over a period of time;
a nebuliser and;
a target;
wherein said eluent emitted by said separation device is nebulised, in use, by said nebuliser wherein a stream of analyte droplets are directed to impact upon said target so as to ionise said analyte to form a plurality of analyte ions; and
wherein said mass spectrometer further comprises a control system, wherein said control system is arranged and adapted either: (i) to switch the polarity of said target during a single experimental run; or (ii) to repeatedly switch the polarity of said target during a single experimental run.

19. A method of mass spectrometry comprising:
providing a separation device arranged and adapted to emit an eluent over a period of time;
providing a target; and
nebulising said eluent emitted by said separation device wherein a stream of analyte droplets are directed to impact upon said target so as to ionise said analyte to form a plurality of analyte ions;
wherein said method further comprises providing a control system, wherein said control system is arranged and adapted either: (i) to switch the polarity of said target during a single experimental run; or (ii) to repeatedly switch the polarity of said target during a single experimental run.

* * * * *